(12) United States Patent
Tesluk et al.

(10) Patent No.: US 8,256,459 B2
(45) Date of Patent: *Sep. 4, 2012

(54) FLUID CONDUIT CONNECTOR APPARATUS

(75) Inventors: Christopher Tesluk, Providence, RI (US); Malcolm Bock, Medfield, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/837,742

(22) Filed: Jul. 16, 2010

(65) Prior Publication Data
US 2010/0276619 A1 Nov. 4, 2010

Related U.S. Application Data

(63) Continuation of application No. 12/371,837, filed on Feb. 16, 2009, now Pat. No. 7,810,519, which is a continuation of application No. 10/784,639, filed on Feb. 23, 2004, now Pat. No. 7,490,620.

(51) Int. Cl.
*F16L 37/23* (2006.01)

(52) U.S. Cl. ............... 137/614.05; 251/149.8; 251/148; 602/13; 285/124.5

(58) Field of Classification Search .... 285/124.1–124.5; 251/148, 149.8, 149.6, 118, 120; 602/13; 137/614.02–614.06, 613.5
See application file for complete search history.

(56) References Cited

U.S. PATENT DOCUMENTS

| 950,263 A * | 2/1910 | Harpster ............... 251/117 |
| 1,608,239 A | 11/1926 | Rosett |
| 1,670,318 A | 5/1928 | Shaff |
| 1,695,848 A | 12/1928 | Higgins |
| 1,883,240 A | 10/1932 | Phelan |
| 2,280,485 A | 4/1942 | Harris |
| 2,628,850 A | 2/1953 | Summerville |
| 2,638,915 A | 5/1953 | Mitchell |
| 2,694,395 A | 11/1954 | Brown |
| 3,057,001 A | 10/1962 | Rapata |
| 3,287,031 A | 11/1966 | Simmons et al. |
| 3,469,863 A | 9/1969 | Riester et al. |
| 3,728,875 A | 4/1973 | Hartigan et al. |
| 3,733,577 A | 5/1973 | Hammond |
| 4,013,069 A | 3/1977 | Hasty |
| 4,029,087 A | 6/1977 | Dye et al. |

(Continued)

FOREIGN PATENT DOCUMENTS

DE 19846922 A1 4/2000

(Continued)

OTHER PUBLICATIONS

Tyco Healthcare Kendall, SCD Response Catalog, Mar. 2000, pp. 1-2.

(Continued)

*Primary Examiner* — John Fristoe, Jr.
*Assistant Examiner* — Andrew J Rost
(74) *Attorney, Agent, or Firm* — Thomas M. Johnston, Esq.

(57) ABSTRACT

A fluid conduit connector apparatus that approximates pneumatic characteristics of a removed pneumatic system component when a fluid conduit is removed from a pneumatic system. The fluid conduit connector apparatus includes a port portion having a valve disposed therein. The valve closes to provide a reduced fluid orifice when a fluid conduit is removed from the port. The reduced fluid orifice is configured to provide pneumatic characteristics of the device being disconnected.

12 Claims, 11 Drawing Sheets

U.S. PATENT DOCUMENTS

| | | |
|---|---|---|
| 4,030,488 A | 6/1977 | Hasty |
| 4,066,084 A | 1/1978 | Tillander |
| 4,091,804 A | 5/1978 | Hasty |
| 4,156,425 A | 5/1979 | Arkans |
| 4,198,961 A | 4/1980 | Arkans |
| 4,207,875 A | 6/1980 | Arkans |
| 4,207,876 A | 6/1980 | Annis |
| 4,253,449 A | 3/1981 | Arkans et al. |
| 4,280,485 A | 7/1981 | Arkans |
| 4,355,632 A | 10/1982 | Sandman |
| 4,580,816 A | 4/1986 | Campbell et al. |
| 4,624,248 A | 11/1986 | Poole et al. |
| 4,696,289 A | 9/1987 | Gardner et al. |
| 4,754,993 A | 7/1988 | Kraynick |
| 4,762,121 A | 8/1988 | Shienfeld |
| 4,762,504 A | 8/1988 | Michaels et al. |
| 4,804,208 A | 2/1989 | Dye |
| RE32,939 E | 6/1989 | Gardner et al. |
| 4,867,699 A | 9/1989 | Oda et al. |
| 4,872,736 A | 10/1989 | Myers et al. |
| 5,007,411 A | 4/1991 | Dye |
| 5,022,387 A | 6/1991 | Hasty |
| 5,031,604 A | 7/1991 | Dye |
| 5,041,025 A | 8/1991 | Haitmanek |
| 5,176,406 A | 1/1993 | Straghan |
| 5,186,163 A | 2/1993 | Dye |
| 5,211,192 A | 5/1993 | Jorgensen |
| 5,217,384 A | 6/1993 | Merten et al. |
| 5,219,185 A | 6/1993 | Oddenino |
| 5,249,830 A | 10/1993 | Calmettes et al. |
| 5,273,254 A | 12/1993 | McNaughton et al. |
| 5,312,083 A | 5/1994 | Ekman |
| 5,330,366 A | 7/1994 | Tsuji et al. |
| 5,354,260 A | 10/1994 | Cook |
| 5,370,423 A | 12/1994 | Guest |
| 5,383,894 A | 1/1995 | Dye |
| 5,387,110 A | 2/1995 | Kantner et al. |
| D357,736 S | 4/1995 | Dye |
| 5,435,009 A | 7/1995 | Schild et al. |
| 5,437,610 A | 8/1995 | Cariapa et al. |
| 5,443,289 A | 8/1995 | Guest |
| D363,988 S | 11/1995 | Dye |
| 5,478,119 A | 12/1995 | Dye |
| 5,575,762 A | 11/1996 | Peeler et al. |
| 5,588,954 A | 12/1996 | Ribando et al. |
| 5,588,955 A | 12/1996 | Johnson, Jr. et al. |
| 5,591,200 A | 1/1997 | Cone et al. |
| 5,626,556 A | 5/1997 | Tobler et al. |
| 5,711,757 A | 1/1998 | Bryant |
| 5,743,755 A | 4/1998 | Aoki |
| 5,795,312 A | 8/1998 | Dye |
| 5,843,007 A | 12/1998 | McEwen et al. |
| 5,876,359 A | 3/1999 | Bock et al. |
| 5,881,769 A | 3/1999 | Hopson |
| 5,897,142 A | 4/1999 | Kulevsky |
| 5,951,502 A | 9/1999 | Peeler et al. |
| 5,988,704 A | 11/1999 | Ryhman |
| 5,989,204 A | 11/1999 | Lina |
| 5,997,495 A | 12/1999 | Cook et al. |
| 6,007,559 A | 12/1999 | Arkans |
| 6,062,244 A | 5/2000 | Arkans |
| 6,105,933 A | 8/2000 | Kanno et al. |
| 6,129,688 A | 10/2000 | Arkans |
| 6,152,495 A | 11/2000 | Hoffmann et al. |
| 6,231,532 B1 | 5/2001 | Watson et al. |
| 6,238,230 B1 | 5/2001 | Sadler et al. |
| 6,257,626 B1 | 7/2001 | Campau |
| 6,257,627 B1 | 7/2001 | Fujiwara et al. |
| 6,290,662 B1 | 9/2001 | Morris et al. |
| 6,319,215 B1 | 11/2001 | Manor et al. |
| 6,394,131 B1 | 5/2002 | Fross et al. |
| 6,423,053 B1 | 7/2002 | Lee |
| 6,436,064 B1 | 8/2002 | Kloecker |
| 6,440,093 B1 | 8/2002 | McEwen et al. |
| 6,468,237 B1 | 10/2002 | Lina |
| 6,494,852 B1 | 12/2002 | Barak et al. |
| 6,537,099 B2 | 3/2003 | Herlinger et al. |
| 6,544,202 B2 | 4/2003 | McEwen et al. |
| 6,547,284 B2 | 4/2003 | Rose et al. |
| 6,592,534 B1 | 7/2003 | Rutt et al. |
| 6,629,941 B1 | 10/2003 | Ishibashi et al. |
| 6,890,204 B2 | 5/2005 | Yamawaki |
| 7,478,840 B2 | 1/2009 | Youssefifar |
| 7,490,620 B2 | 2/2009 | Tesluk et al. |
| 2003/0075923 A1 | 4/2003 | Lepoutre |

FOREIGN PATENT DOCUMENTS

| | | |
|---|---|---|
| EP | 0861651 A1 | 9/1998 |
| GB | 2313784 A | 12/1997 |
| WO | 2004011842 A1 | 2/2004 |

OTHER PUBLICATIONS

Tyco Healthcare Kendall, SCD Soft Sleeve Catalog, Apr. 2001, pp. 1-2.

The Kendall Company, Vascular Therapy Products Catalog, Jan. 1996, pp. 8-5 through 8-7.

The Kendall Company, "The New SCD Compression Sleeve", Aug. 1993, pp. 1-2.

Tyco Healthcare Kendall, "Prevention Gets Personal", Mar. 2001, pp. 1, 2, 4.

Kendall SCD, "Sequential Compression Sleeves", Patent information, Jan. 1993, 6 pages.

PCT International Search Report issued in Application No. PCT/US2005/005599, May 25, 2005, 4 pages.

PCT International Search Report issued in Application No. PCT/US2005/005598, Jun. 2, 2005, 5 pages.

PCT International Search Report issued in Application No. PCT/US2005/005600, Jun. 2, 2005, 7 pages.

PCT Invitation to Pay Additional Fees issued in Application No. PCT/US2005/005679, Jun. 10, 2005, 6 pages.

\* cited by examiner

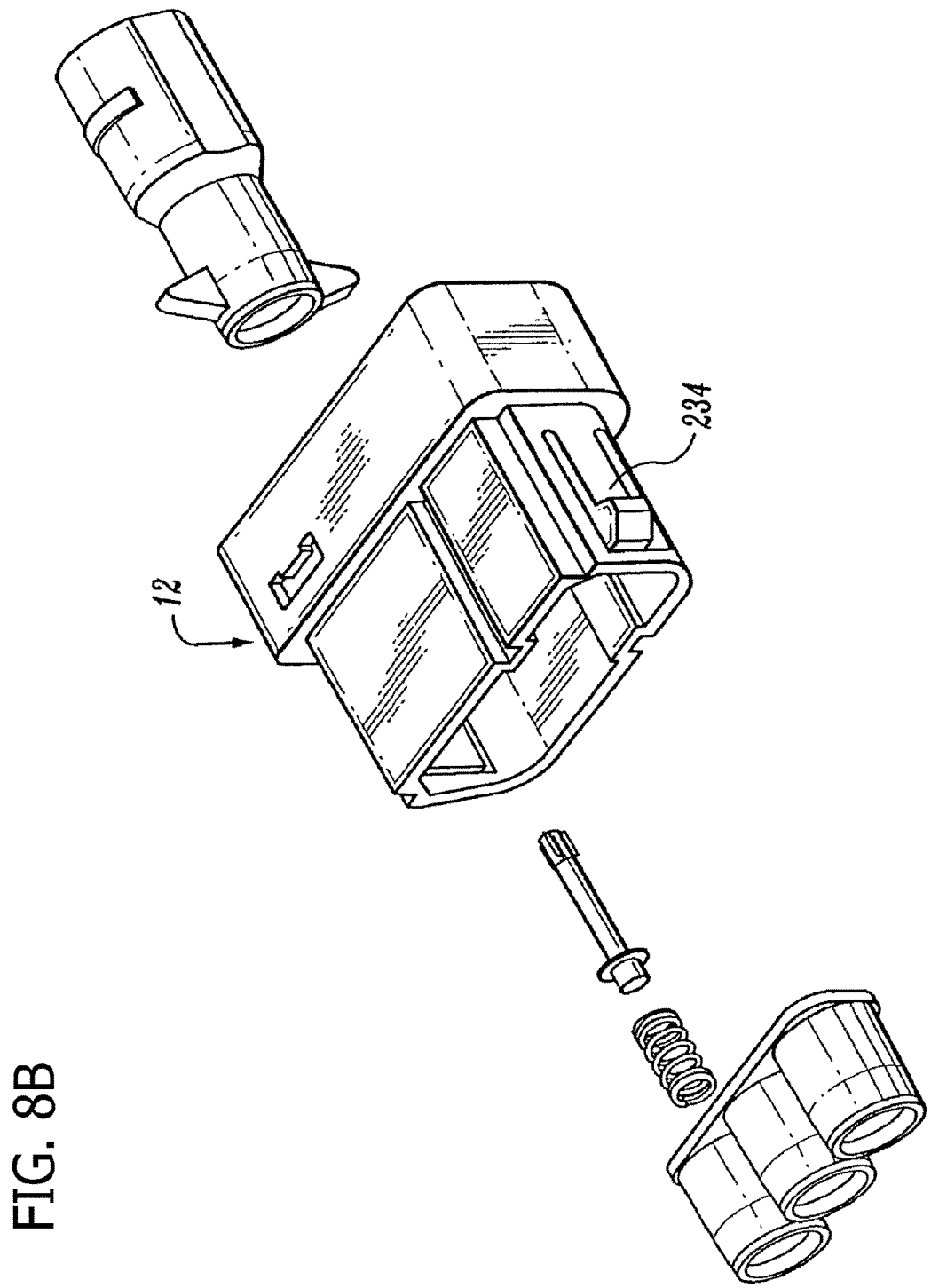

FLUID CONDUIT CONNECTOR APPARATUS

CROSS-REFERENCE OF RELATED APPLICATIONS

This is a continuation of co-pending U.S. patent application Ser. No. 12/371,837 filed Feb. 16, 2009, which is a continuation of U.S. patent application Ser. No. 10/784,639, filed Feb. 23, 2004, and issued as U.S. Pat. No. 7,490,620, the entireties of which are hereby incorporated by reference.

FIELD OF THE INVENTION

The present disclosure generally relates to the field of fluid conduit connectors for application to multiple fluid line systems and more particularly to fluid line connectors having a valved port.

BACKGROUND OF THE INVENTION

Medical conditions that form clots in the blood, such as deep vein thrombosis (DVT) and peripheral edema, are a major concern to immobile medical patients. Such patients include those undergoing surgery, anesthesia, extended periods of bed rest, etc. These blood clotting conditions generally occur in the deep veins of the lower extremities and/or pelvis. These veins, such as the iliac, femoral, popiteal and tibial return deoxygenated blood to the heart. When blood circulation in these veins is retarded due to illness, injury or inactivity, there is a tendency for blood to accumulate or pool. A static pool of blood provides an ideal environment for dangerous clot formations. A major risk associated with this condition is interference with cardiovascular circulation. Most seriously, a fragment of the blood clot can break loose and migrate. A pulmonary emboli can form a potentially life-threatening blockage in a main pulmonary artery.

The conditions and resulting risks associated with patient immobility can be controlled or alleviated by applying intermittent pressure to a patient's limb to assist in blood circulation. Known devices such as one piece pads and compression boots have been employed to assist in blood circulation. See, for example, U.S. Pat. Nos. 6,290,662 and 6,494,852.

Sequential compression devices have been used, which consist of an air pump connected to a disposable wraparound pad by a series of fluid conduits such as air tubes, for example. The wraparound pad is placed around the patient's leg. Air is then forced into different parts of the wraparound pad in sequence, creating pressure around the calves and improving venous return. These known devices suffer from various drawbacks due to their bulk and cumbersome nature of use. These drawbacks cause patient discomfort, reduce compliance and can prevent mobility of the patient as recovery progresses after surgery. It would be desirable to overcome the disadvantages of such known devices with a compression apparatus that employs a fluid connector apparatus in accordance with the principles of the present disclosure.

SUMMARY OF THE INVENTION

In one aspect of the present invention, a fluid connector apparatus adapted for use with a compression apparatus generally comprises a first connector including a first plurality of fluid ports each having proximal ends and distal ends. At least one of the fluid ports comprises a coupling port having a port seat therein defining a fluid orifice. The first connector is adapted for nondestructive, releasable connection with a second connector at a distal end of the first connector. Each fluid port has a fluid conduit connected to a proximal end of a respective one of the fluid ports. A first of the fluid conduits is connected to the coupling port. A coupling fitting is connected to the first fluid conduit and is removably mated with the coupling port thereby to connect the first fluid conduit to the coupling port. A valve is disposed in the coupling port for movement relative to the coupling port. The valve is operatively engaged with the coupling fitting when the coupling fitting is mated with the coupling port of the first connector to move and hold the valve away from the fluid orifice. The valve is disengaged from the coupling fitting when the coupling fitting is removed from the coupling port of the first connector. The valve moves upon removal of the coupling fitting from the coupling port into engagement with the port seat to reduce a dimension of the fluid orifice without completely closing the fluid orifice.

Other objects and features will be in part apparent and in part pointed out hereinafter.

BRIEF DESCRIPTION OF THE DRAWINGS

FIG. 8B is a perspective view of the first connector shown in FIG. 8A and an alternate embodiment of the second connector shown in FIG. 2;

Corresponding reference characters indicate corresponding parts throughout the drawings.

DESCRIPTION OF THE PREFERRED EMBODIMENTS

The exemplary embodiments of the fluid conduit connector apparatus and methods of operation disclosed are discussed in terms of prophylaxis compression apparatus and vascular therapy including a prophylaxis compression apparatus for application to a limb of a body and more particularly in terms of a compression apparatus having removable portions. It is envisioned that the present disclosure, however, finds application with a wide variety of pneumatic systems having removable fluid conduits, such as, for example, medical and industrial applications requiring timed sequences of compressed air in a plurality of air tubes.

In the discussion that follows, the term "proximal" refers to a portion of a structure that is closer to a torso of a subject and the term "distal" refers to a portion that is further from the torso. As used herein the term "subject" refers to a patient undergoing vascular therapy using the prophylaxis sequential compression apparatus. According to the present disclosure, the term "practitioner" refers to an individual administering the prophylaxis sequential compression apparatus and may include support personnel.

The following discussion includes a description of the fluid conduit connector apparatus, followed by a description of an exemplary method of operating the fluid conduit connector apparatus in accordance with the principals of the present disclosure. Reference will now be made in detail to the exemplary embodiments and disclosure, which are illustrated with the accompanying figures.

Figure 1:
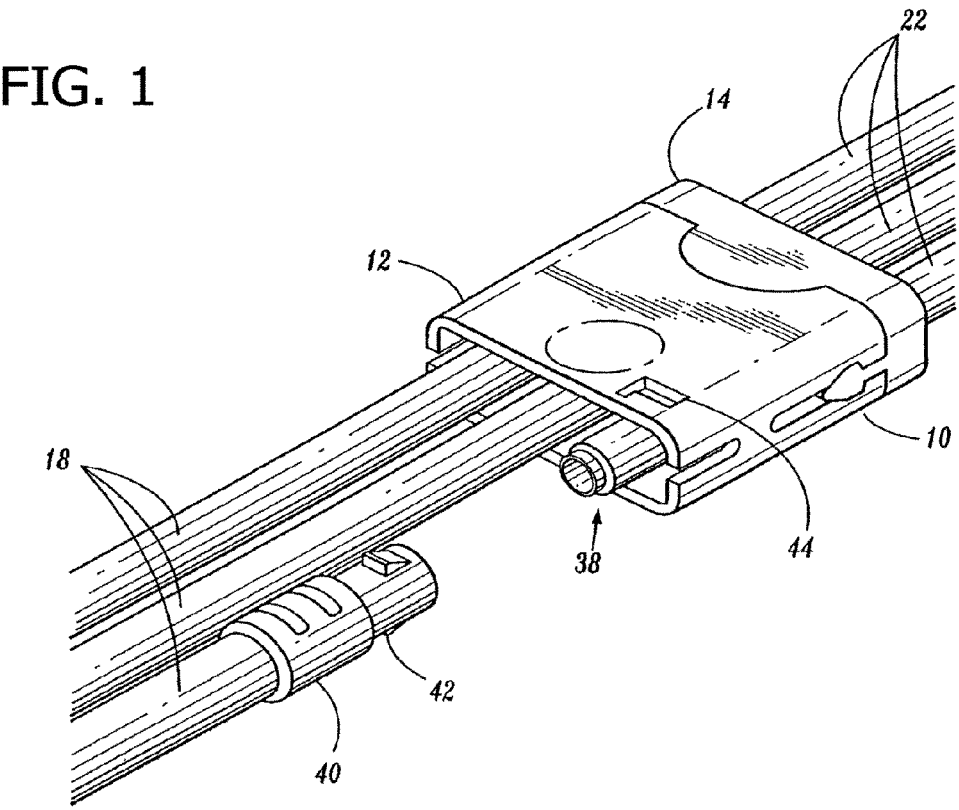
FIG. 1 is a perspective view of an illustrative embodiment of a fluid conduit connector apparatus in accordance with the principles of the present disclosure.
Figure 2:
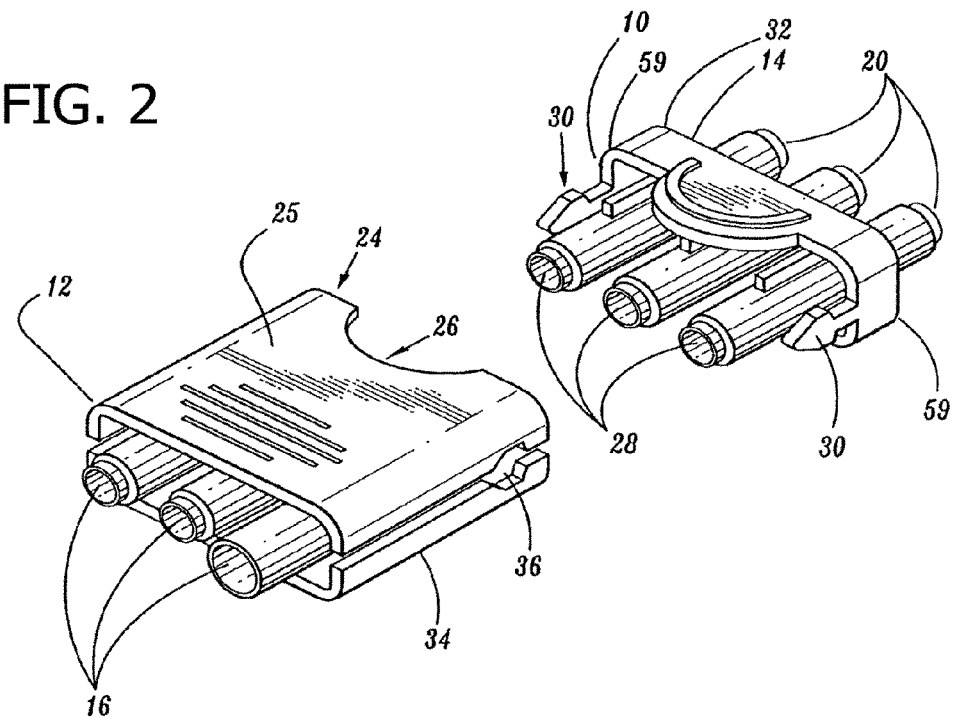
FIG. 2 is a perspective view of a first and second connector according to an illustrative embodiment of the fluid conduit connector apparatus of the present disclosure.
Figure 3:
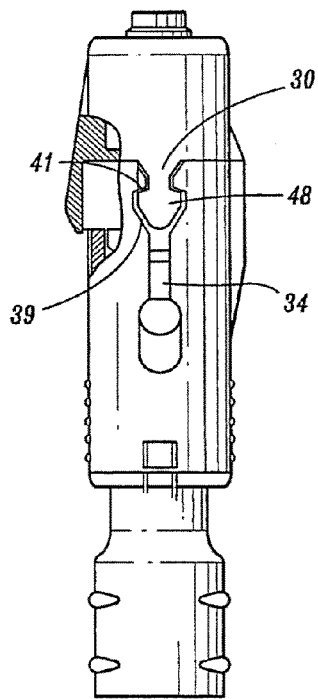
FIG. 3 is a side partial cross-sectional view of the illustrative fluid conduit connector apparatus shown in FIG. 1.
Figure 4:
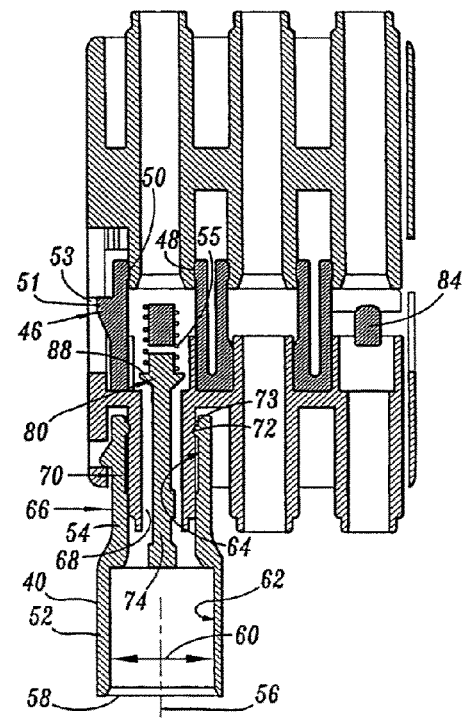
FIG. 4 is a top cross sectional view of the illustrative fluid conduit connector apparatus shown in FIG. 1.
Figure 5:
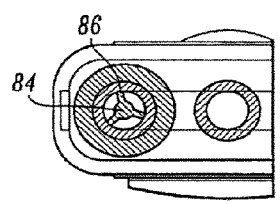
FIG. 5 is front cross sectional view of the coupling port in an illustrative fluid conduit connector apparatus according to the present disclosure.

Turning now to the figures, wherein like components are designated by like reference numerals throughout the several views. Referring initially to FIGS. 1 and 2, there is illustrated a fluid conduit connector apparatus 10, constructed in accordance with the principals of the present disclosure. The fluid conduit connector apparatus 10 includes a connector having a first connector 12 and second connector 14. First connector 12 is configured for removable engagement with a second connector 14.

Figure 15:
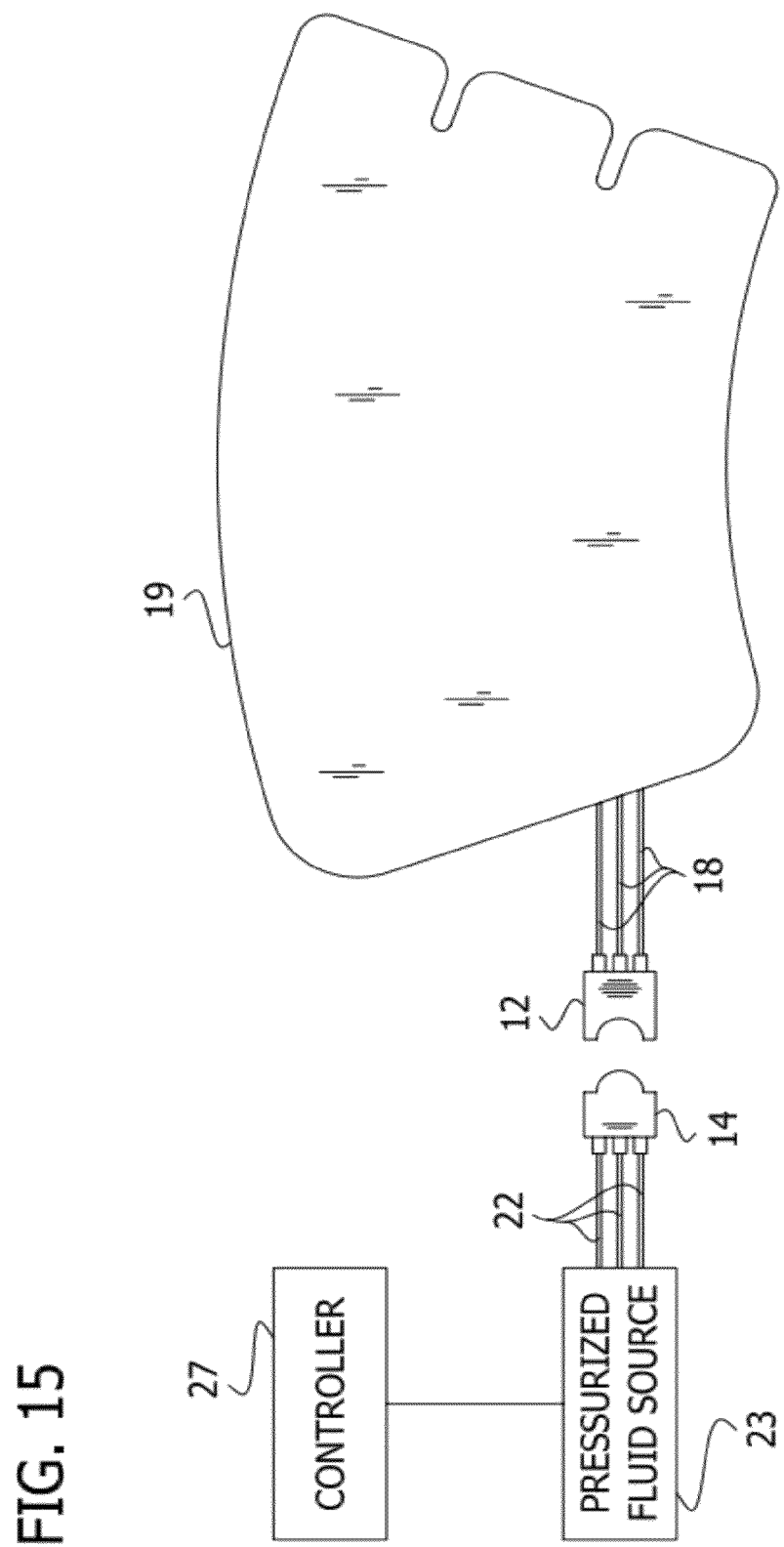
FIG. 15 is a diagrammatic view of a controller and fluid pressure source used with the fluid conduit connector apparatus.

The first connector 12 includes a first plurality of fluid ports 16 extending proximally therefrom and adapted for receiving a first plurality of fluid conduits 18. Fluid conduits 18 are connected to a compression apparatus, including for example, a compression sleeve 19 (see FIG. 15) adapted for disposal and treatment about a limb of a subject (not shown). The second connector 14 includes a second plurality of fluid ports 20 extending distally therefrom and adapted for receiving a second plurality of fluid conduits 22. Fluid conduits 22 fluidly communicate with a pressurized fluid source 23 that is adapted to inflate the compression sleeve via the advantageous configuration of fluid conduit connector apparatus 10, as described in accordance with the principles of the present disclosure. The pressurized fluid source 23 is controlled by a controller 25 that includes instructions providing a timed sequence of the pressurized fluid to the compression sleeve 19. It is envisioned that conduits 18, 22 may include various tubing such as, for example, non-webbed tubing, etc.

The fluid ports 16, 20 of connectors 12, 14 respectively, each define an inner fluid orifice or passageway that facilitate fluid communication between connectors 12, 14. In turn, connectors 12, 14 facilitate fluid communication between the pressurized fluid source and the compression sleeve. Although the fluid conduit connector apparatus 10 is illustrated as having a set of three fluid ports in each connector for connecting sets of three fluid conduits, it is contemplated that each connector can have any number of fluid ports without departing from the scope of the present disclosure.

The first connector 12 includes a sleeve 24 defining a cavity 26 having a distal opening. The cavity 26 houses distal portions of the first plurality of fluid ports 16 which extend distally within the cavity 26. The second connector 14 includes a plurality of fluid couplings 28 extending proximally therefrom. The plurality of fluid couplings 28 is formed by proximal portions of the second plurality of fluid ports 20 for alignment with the distal portions of the first plurality of fluid ports 16. A locking arm 30 extends proximally from the body portion 32 of the second connector 14. A slot 34 in the sleeve 24 of first connector 12 includes a window 36 adapted for removably accepting the locking arm 30 to retain the first connector 12 to the second connector 14.

At least one of the first plurality of ports is a coupling port 38 adapted for receiving a coupling fitting 40. The coupling fitting 40 is permanently attached to the distal end of a corresponding one of the first plurality of fluid conduits 18. A locking tab extending radially from the coupling fitting 40 is configured for engaging a detent cavity 44 in the first connector 12, for example in the sleeve 24 as shown in FIG. 1. A streamlined outer surface 25 prevents the connectors from snagging on patient clothing or bedding.

Referring now to FIGS. 3-7, the various components of the fluid conduit connector apparatus will be described in further detail.

A gasket 46 conforms to the space between the plurality of couplings 28 and the distal portion of the first plurality of fluid ports 16 within the cavity 26 when the first 12 is engaged with the second connector 14. The gasket 46 provides sealing for pressurized fluid communication between corresponding fluid conduits by providing a sealed fluid channel including the first plurality of fluid ports and second plurality of fluid ports. It is envisioned that the gasket 46 can be efficiently and inexpensively manufactured using a variety of common materials or fabrication methods, for example by injection molding an elastomeric material or dye cutting a cork or paper based gasket material. It is envisioned that the gasket 46 can be configured for retention to one or the other of the first connector 12 and second connector 14. In the illustrative embodiment, the gasket includes a proximal lip 48 configured to engage the distal portion of each of the first plurality of fluid ports to provide fluid sealing between the first connector 12 and the second connector 14. The gasket includes a retention portion extending therefrom. The sleeve 24 includes a gasket retention groove adapted to accept the retention portion and thereby retain the gasket to the sleeve 24 when the second connector 14 is removed therefrom.

The slot 34 at least partially bifurcates the sleeve 24 to allow spreading of the sleeve 24 under stress when the locking arm 30 is pressed into the slot 34 at its distal end as the first connector 12 is mated to the second connector 14. When an engagement portion 48 of the locking arm 30 reaches the window portion 36 of the slot 34 the sleeve returns to its relaxed shape to releasably retain the second connector 14 by its locking arms 30. The locking arm 48 is formed with a leading surface 39 inclined at an angle (i.e., first angle) and a trailing surface 41 inclined at a second angle. In the illustrative embodiment, the leading surface 39 is inclined at a shallower angle than the trailing 41 surface so that the force to connect the first connector 12 to the second connector 14 is lighter than the force to disconnect the first connector 12 from the second connector 14. Predetermined connection/disconnection forces can thereby be achieved by proper selection of the first and second angle when designing a particular locking arm 48.

Figure 8:
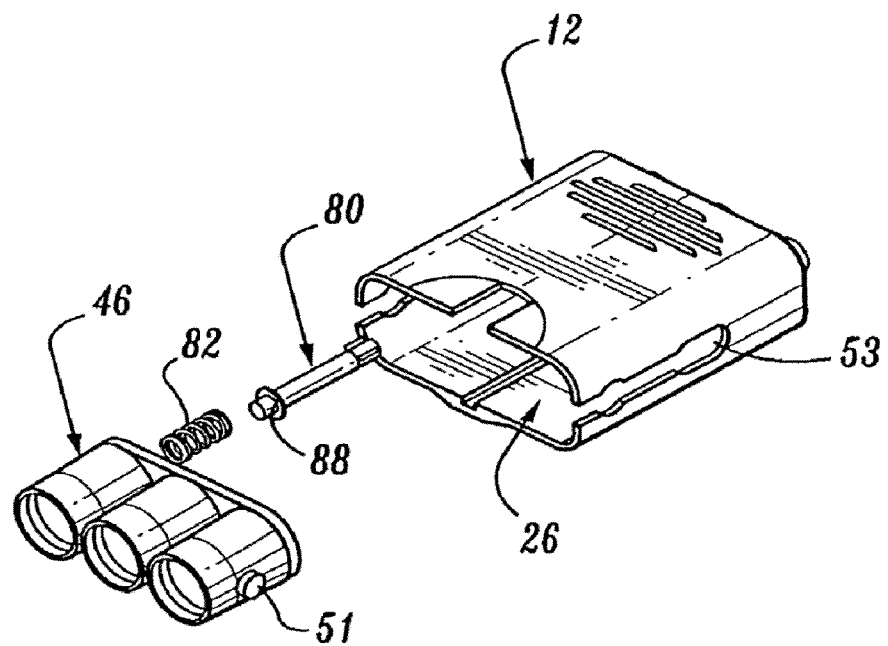
FIG. 8 is an exploded view of the various components of an illustrative first connector in a fluid conduit connector apparatus according to the present disclosure.
Figure 8A:
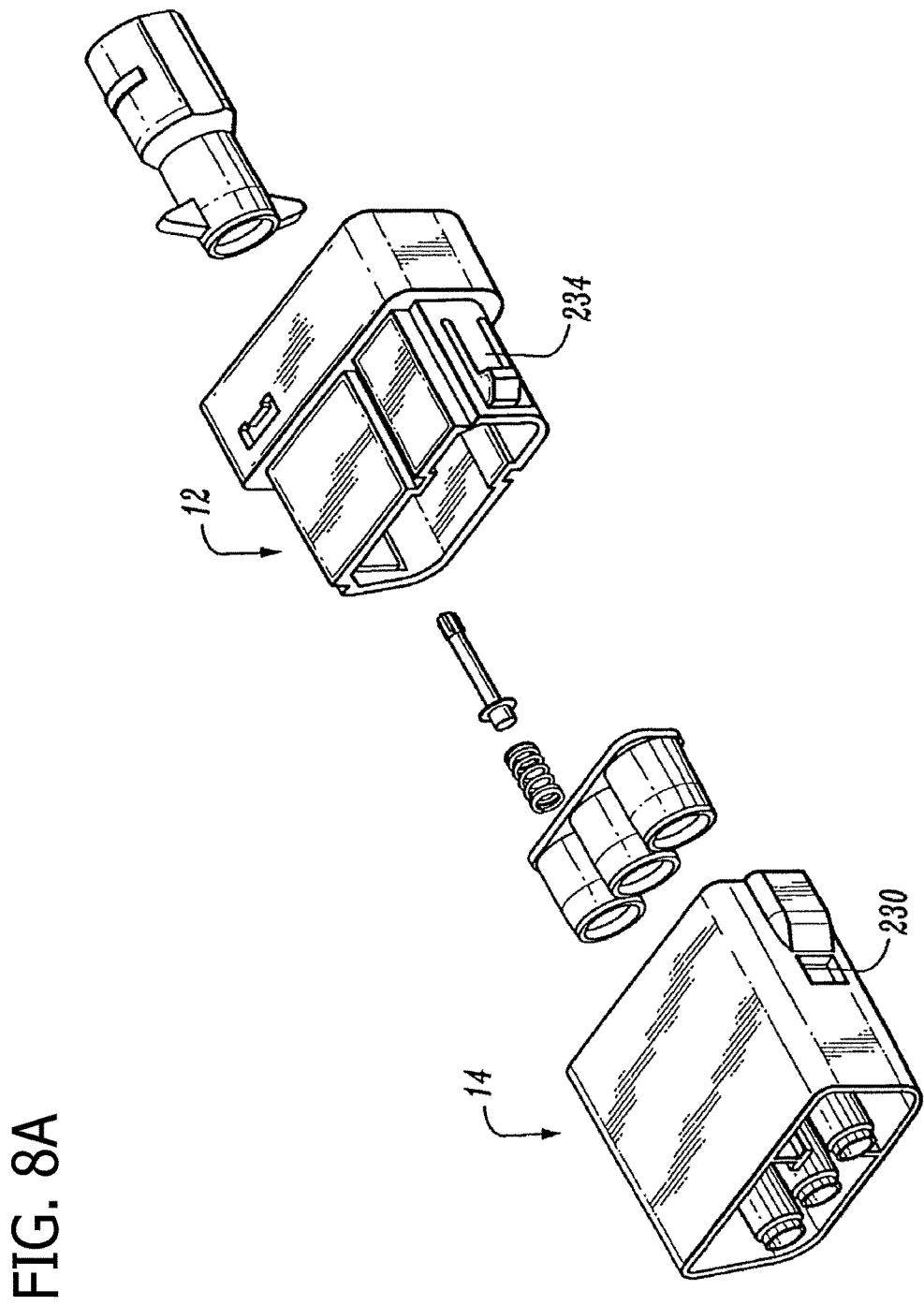
FIG. 8A is a perspective view of an alternate embodiment of the first connector shown in FIG. 8.
Figure 8C:
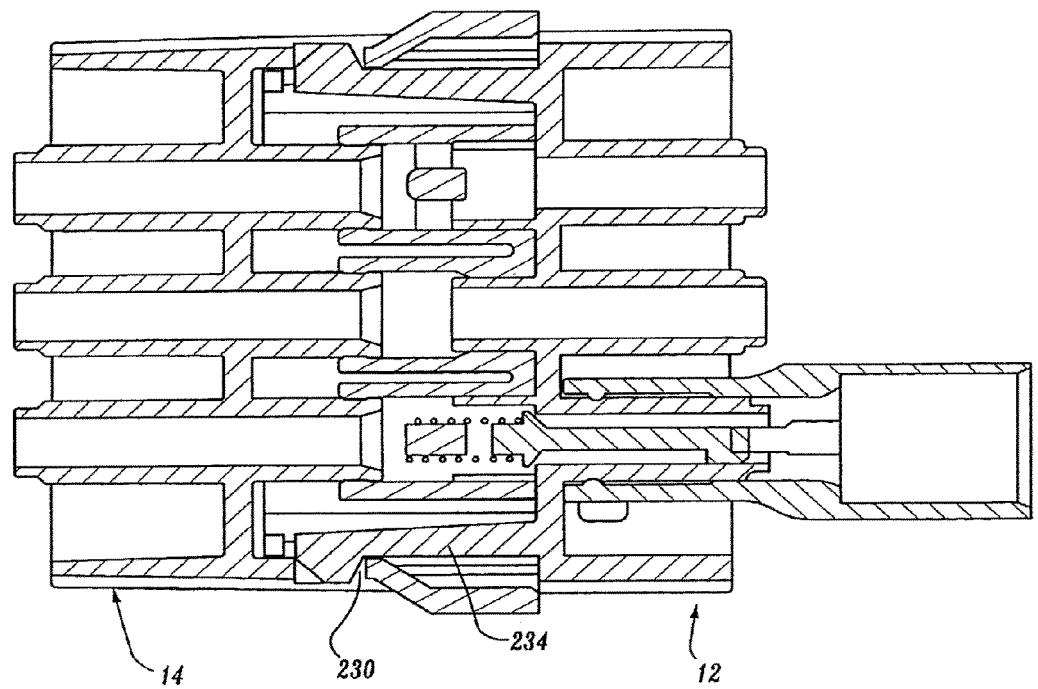
FIG. 8C is a cross-sectional plan view of the first connector and the second connector shown in FIG. 8B.

Although the illustrative embodiment described herein refers to a particular locking arm and slot configuration, it is envisioned that virtually any type of removable retention method may be used to removably retain the first connector to the second connector without departing from the scope of the present disclosure. For example, an interference fit may be provided between the first connector 12 and second connector 14 or may be provided by a properly configured deformable gasket 46. Alternatively, a snap or detent arrangement known in the art may be used to retain the first connector 12 to the second connector 14. For example, as shown in FIGS. 8A, 8B and 8C, first connector 12 includes a locking arm 234 that is configured for mating engagement with corresponding slot 230 formed in second connector 14, similar to the arm and slot structure described.

An alignment rib 59 (FIG. 1) extends radially from at least one of the plurality of couplings 28 along its longitudinal axis. A corresponding alignment slot (not shown) is provided in the inner surface of the sleeve 24 extending to the distal end thereof for accepting the alignment rib 59. It is contemplated that virtually any type of alignment rib/slot configuration commonly used in the art of for alignment of mating connectors can be used without departing from the scope of the present disclosure.

The coupling fitting 40 includes a proximal cylinder 52 and a distal cylinder 54 aligned along a longitudinal axis 56. The proximal cylinder 52 includes a proximal opening 58 and an inside diameter 60 defining an inner surface 62 configured for a press fit corresponding to the outside diameter of one of the first plurality of fluid conduits 18. In the illustrative embodiment, the corresponding fluid conduit is an air tube which is press fit into the proximal cylinder 52 through its proximal opening 58. In an illustrative embodiment, the fluid conduit is substantially permanently attached to the proximal cylinder 52 by friction. In alternative embodiments a variety of suitable adhesives may be applied to the inner surface 62 of the proximal cylinder 52 to permanently attach the fluid conduit and provide a fluid tight seal therebetween. For example, it is envisioned that a silicon adhesive, rubber cement, a material specific adhesive compound, an o-ring, a gasket or the like can be used according to methods well known in the art to attach the fluid conduit to the coupling fitting.

The distal cylinder 54 comprises an inner surface defined by an inside contour 64 revolved about the longitudinal axis 56 and an outer surface 66 defined by an outside diameter. In the illustrative embodiment, the inside contour 64 includes a sealing portion 68, a flexing portion 70 and an annular lip portion 72. The sealing portion 68 has an inside diameter adapted for a tight fit against the outside surface of the coupling port 38 to provide at least partial fluid sealing therebetween. The annular lip portion 72 defines an annular ring that compresses against the outside surface of coupling port 38 and provides fluid sealing therebetween. The flexing portion 70 is defined by a reduced wall thickness which allows the distal cylinder 54 to deflect inwardly to facilitate engagement of the locking tab 42 to the detent cavity 44.

Although the illustrative embodiment is described with respect to a particular retention and sealing configuration between the coupling fitting 40 and coupling port 38, it is envisioned that virtually any type of coupling fitting retention and sealing method known in the art can be used between the coupling fitting 40 and the external surface of the coupling port 38 without departing from the scope of the present disclosure. For example, it is envisioned that a threaded collar, a cantilever snap arm or the like can be used for attachment of the coupling fitting 40 to the coupling port 38 or to the first connector 12.

Figure 9:
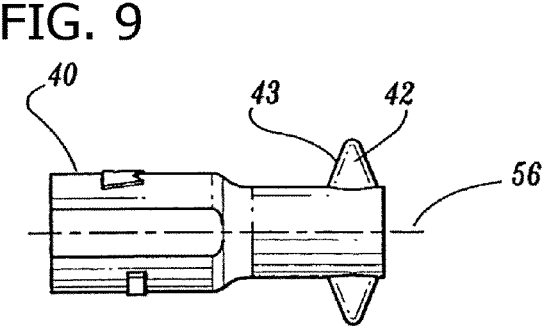
FIG. 9 is a side view of an illustrative coupling fitting according to the present disclosure.
Figure 10:
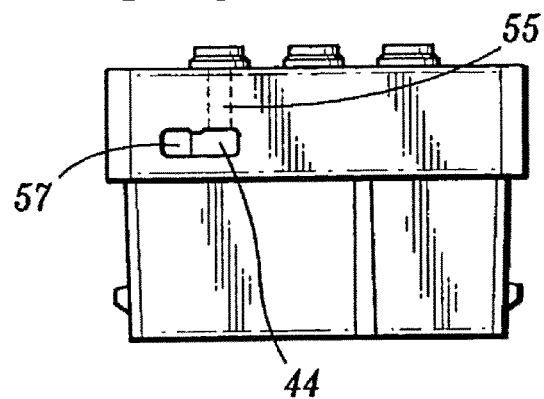
FIG. 10 is a top view of a first or second connector including a detent cavity according to an illustrative embodiment of the present disclosure.

In another example referring to FIGS. 9 and 10, the sleeve 24 or interior surface of the first connector 12 can include a detent cavity 44 extending at least partially into the interior surface and adapted for accepting the locking tab 42 of the coupling fitting 40. A detent 57 of tab 42 is inserted into sleeve 24 to become disposed in cavity 44. Detent 57 is rotated through cavity 44, via manipulation of fitting 40 and retained in position by bump formed in the wall of cavity 44. In an alternate embodiment, the detent cavity shown in FIG. 10 includes a longitudinal track portion 55 (shown in phantom) adapted for guiding the locking tab 42 (FIG. 9) during engagement and disengagement and an annular portion 57 adapted for retaining the locking tab 42 (FIG. 9) when the coupling fitting 40 is rotated about its longitudinal axis 56. Along its length, the detent cavity 44 can have varying depth or width into the interior surface. The varying depth of the detent cavity 44 provides a predetermined engagement/disengagement force/displacement profile between the locking tab 42 and the detent cavity. In one embodiment, the locking tab has an outer portion with an enlarged manual engagement surface 43 to assist manipulation of the locking tab 42.

In an illustrative embodiment of the invention, the coupling fitting includes an engagement portion 74 adapted for opening a valve 76 disposed within the coupling port 38. The engagement portion 74 extends distally from a transverse wall 78 within the coupling fitting 40 to displace a plunger 80 in the valve 76. In the illustrative embodiment, the transverse wall 78 is disposed within the coupling fitting 40 about between the proximal cylinder 52 and the distal cylinder 54 and orthogonal to the longitudinal axis 56. At least one fluid passageway extends through the transverse wall.

Although the illustrative embodiment is described in terms of a distally extending engagement portion, it is envisioned that virtually any type of valve engagement structure can be used to displace a valve plunger 80 within the scope of the present disclosure. For example, a flat surface of the transverse wall 78 or a rib extending from the inner surface of the distal cylinder 54, can be aligned with a complementary structure within a valve 76 to displace a valve plunger 80 when the coupling fitting 40 is engaged with the coupling port 38.

The illustrative embodiment includes a valve 76 is disposed within the coupling port 38. The valve 76 includes a plunger 80 movable along the longitudinal axis of the coupling port 38 and biased proximally by a spring 82. The spring 82 is supported by the gasket 46 which is held in place in cavity 26 by protrusion 51 on the gasket 46. Adhesive may alternatively be used to maintain gasket 46 in position. The gasket 46 includes a spring seat formed along the longitudinal axis of any gasket passageway to be aligned with a coupling port. (FIGS. 4-5) The spring seat in the illustrative embodiment includes a central stub 84 supported by radial spars 86 within the gasket opening.

Figure 7:
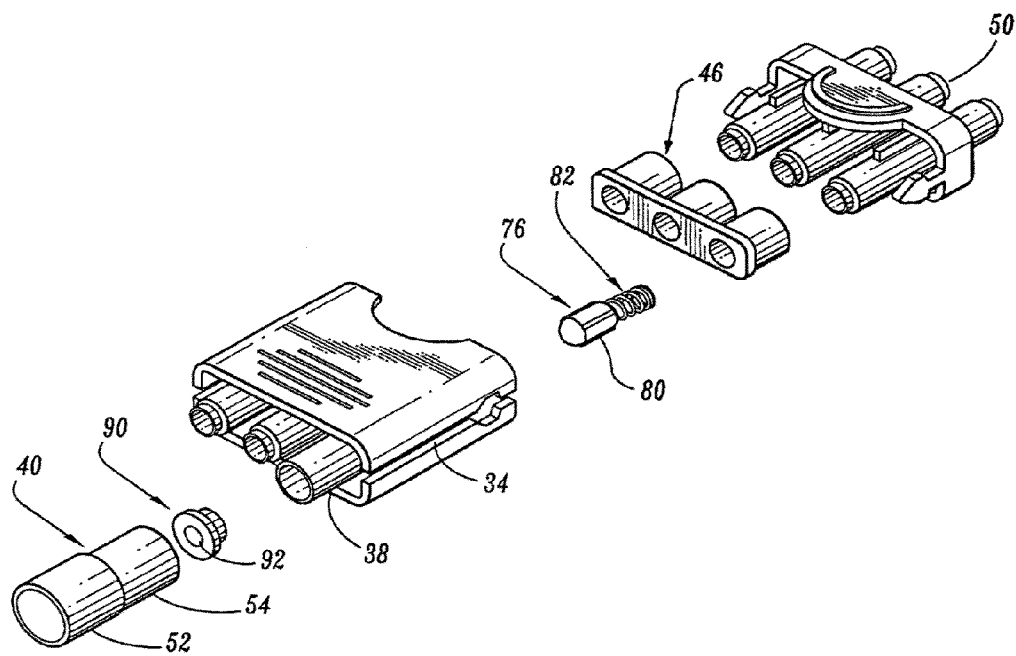
FIG. 7 is an exploded view of the various components of an illustrative fluid conduit connector apparatus according to the present disclosure.

The valve can be easily assembled by installing the spring 82 over the distal end of the plunger 80 to form a plunger and spring sub-assembly. The plunger 80 includes a step 88 to engage the proximal end of the spring 82. The plunger and spring sub-assembly can then be installed into the coupling port 38 from its proximal end. The gasket 46 can then be installed into the cavity 26. Alternatively, the plunger and spring sub-assembly can be installed to the gasket 46 by fitting the spring 82 to the spring seat before installing the gasket 46 spring 82 and plunger 80 together to the first connector 12. FIGS. 7 and 8 provide two illustrative embodiments of a plunger 80 according to the present disclosure.

Although the present disclosure illustrates the use of a coil spring 82 to bias the plunger 80, it is contemplated that virtually any type of plunger and spring arrangement known in the art can be used to provide biasing of the plunger 80 within the scope of the present disclosure. For example, it is envisioned that spring force could be applied to the plunger 80 by forming a plastic cantilever spring arm that could be formed within the first connector 12. Alternatively a structure similar to the spring seat could be formed of elastomeric material as part of the gasket 46 to provide a biasing force to the plunger 80 without departing from the scope of the present disclosure.

When the coupling fitting 40 is engaged with the coupling port 38, the engagement portion 74 of the coupling fitting forces the plunger 80 to move distally against the force of the spring 82 which is thereby compressed. An open fluid connection is thereby provided from the fluid conduit connected to the coupling fitting 40, through the coupling port 38 to the corresponding one of the second plurality of fluid conduits 22, i.e., the corresponding air tube.

For example, a portion of the compression sleeve that fluidly communicates with the pressurized fluid source via coupling port 38 may be removed from the remainder of the compression sleeve. The remaining portion of the compression sleeve continues to provide treatment to the limb of the subject. Upon removal of the selected portion, the coupling fitting 40 is disconnected and not engaged to the coupling port 38. Spring 82 forces the plunger 80 to its proximal limit of travel where the plunger 80 engages a proximal stop such that valve 76 is in a closed position.

The plunger 80 is configured to cooperate with an internal structure in the coupling port 38 to define a reduced fluid orifice when the plunger 80 is displaced to its proximal limit. The reduced fluid orifice is designed to provide pneumatic characteristics approximating the pneumatic characteristics of a detached device.

In an illustrative embodiment, (FIGS. 6-7), a cap 90 having a fluid passageway 92 therethrough is disposed in the proximal opening of the coupling port 38. The cap 90 provides a stop defining a proximal limit of plunger travel and is configured to cooperate with the plunger 80 of valve 76, such that valve 76 reduces the dimension of the fluid orifice of coupling port 38.

Figure 6:
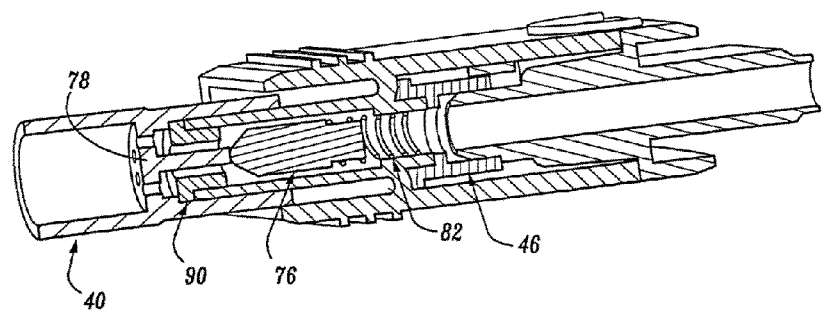
FIG. 6 is a side cross sectional perspective view of the fluid conduit connector apparatus according to an illustrative embodiment of the present disclosure.
Figure 6A:
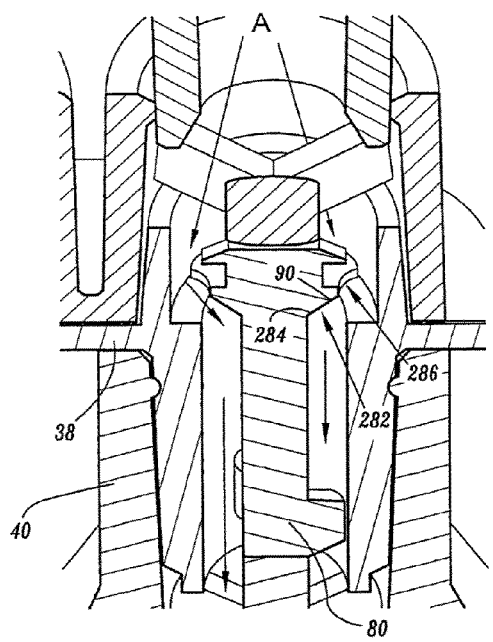
FIG. 6A is a cutaway perspective view of the fluid conduit connector apparatus shown in FIG. 6.
Figure 6B:
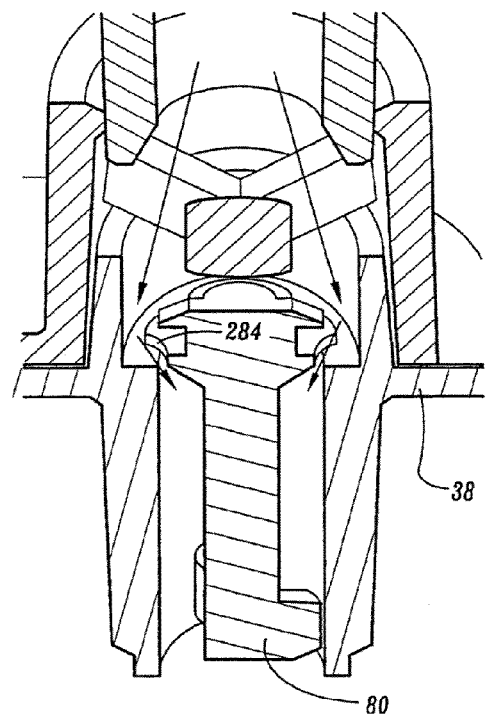
FIG. 6B is a cutaway perspective view of the fluid conduit connector apparatus shown in FIG. 6.

For example, as shown in FIGS. 6A and 6B, coupling fitting 40 is connected to the coupling port 38 to force plunger 80 distally and open the fluid connection (FIG. 6A), described above, for inflating a removable portion of an inflatable compression sleeve (not shown). To provide such an open connection, a valve seat 282 of plunger 80 is disposed via spring 82 (not shown in FIGS. 6A and 6B for clarity), out of engagement with a conical seat 284 of cap 90. This configuration allows air to flow around the conical seat 284 and through conduit 22 (not shown), and out to the inflatable removable portion of the compression sleeve, as shown by arrows A.

For removal of the removable portion of the compression sleeve, coupling fitting 40 is removed from coupling port 38. Spring 82 forces valve seat 282 into engagement with a counter bore edge of conical seat 284. Thus, this configuration advantageously reduces the dimension of the fluid orifice of coupling port 38 such that air only flows through cavities defined by semi-circular slots 286 of valve seat 282 and the bore edge of conical seat 284. Slots 286 are formed on the sides of valve seat 282. The cavities defined by slots 286 and conical seat 284 facilitate fluid flow that approximates the pneumatic behavior of the removable portion of the compression sleeve when coupling fitting 40 is connected to coupling port 38 during an open fluid connection. The cavities defined by slots 286 and conical seat 284 may have various configurations and dimensions including geometries such as, for example, elliptical, polygonal, etc.

This configuration advantageously approximates the pneumatic characteristics of a detached device. It is contemplated that the fluid orifice of coupling port 38 may be variously configured such that corresponding engagement with plunger 80 reduces the orifice dimension to approximate fluid flow through coupling port 38 that would otherwise occur with valve 76 in the open position. It is further contemplated that plunger 80 may includes openings to approximate fluid flow. It is envisioned that valve 76 is operable to reduce the dimension of the fluid orifice of coupling port 38 over a range of closed positions, including partial fluid flow, leakage, etc. to approximate fluid in the port or alternatively, the orifice may completely close to prevent fluid flow through the corresponding port. In a completely closed configuration, pump speed or other settings may be adjusted.

In a particular embodiment, the present disclosure provides an air tubing connector for use with a compression apparatus having removable portions, see, for example, the compression sleeve described in U.S. Pat. No. 7,282,038, filed on Feb. 23, 2004 and entitled Compression Apparatus. Three separate air tube are connected to an ankle portion, a calf portion and a knee portion of the apparatus. Each portion is supplied with a timed sequence of compressed air through its respective air tube. The proximal end of each of the three air tubes is connected to the first plurality of fluid ports 16 in a first connector 12 according to the present disclosure. A mating set of three air tubes extends from a timed pressure source and is connected to the second plurality of fluid ports 18 in a second connector 14 according to the present disclosure.

In the illustrative embodiment, the distal end of the thigh tube is connected to the first connector 12 via a coupling fitting 40 and port 38 as described hereinbefore. When a patient no longer requires the thigh portion of the prophylaxis compression apparatus, the thigh portion can be removed and the tubing attached thereto can be disconnected from the first connector at the coupling port 38. Operation of the valve 76 in the coupling port 38 provides a reduced fluid orifice that restricts airflow therethrough to approximate the pneumatic characteristics of the thigh portion and its corresponding air tube. Thus, sensors in the timed pressure source will not detect a change in fluid pressure or flow rate when the thigh portion is removed. This allows the timed pressure source to continue supplying uninterrupted timed air pressure to the ankle and calf portions of the prophylaxis compression apparatus.

Figure 11:
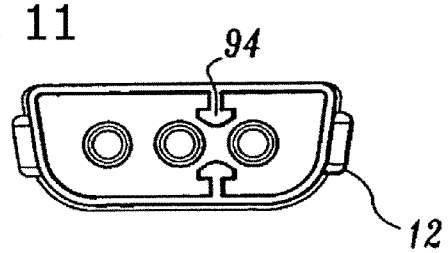
FIG. 11 is a front view of a first or second connector including an interference rib according to an illustrative embodiment of the present disclosure.
Figure 12:
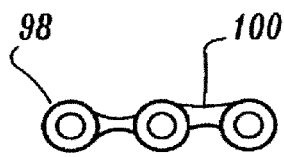
FIG. 12 is a front view of webbed tubing having an increased webbing volume according to an illustrative embodiment of the present.

Referring to FIGS. 11 and 12, certain embodiments are provided wherein the first plurality of fluid conduits 18 is a set of webbed tubing 98 having increased webbing volume 100 between at least one pair of adjacent conduits. At least one interference rib 94 is formed between at least one pair of adjacent fluid ports in the first plurality of fluid ports. The increased webbing volume 100 is aligned with the interference rib 94 if the set of webbed tubing 98 is improperly oriented with the first connector 12. The interference rib 94 thereby prevents attachment of improperly oriented fluid conduits to the first connector 12. Similarly, the second plurality of fluid conduits 22 can include an increased webbing volume configured to interfere with an interference rib between adjacent ports in the second connector 14 to prevent attachment of improperly oriented fluid conduits to the second connector 14.

Figure 13:
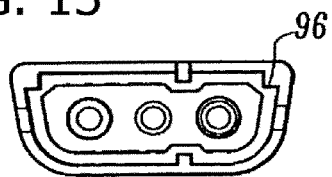
FIG. 13 is an end view of a first or second connector including an interference key according to an illustrative embodiment of the present disclosure.
Figure 14:
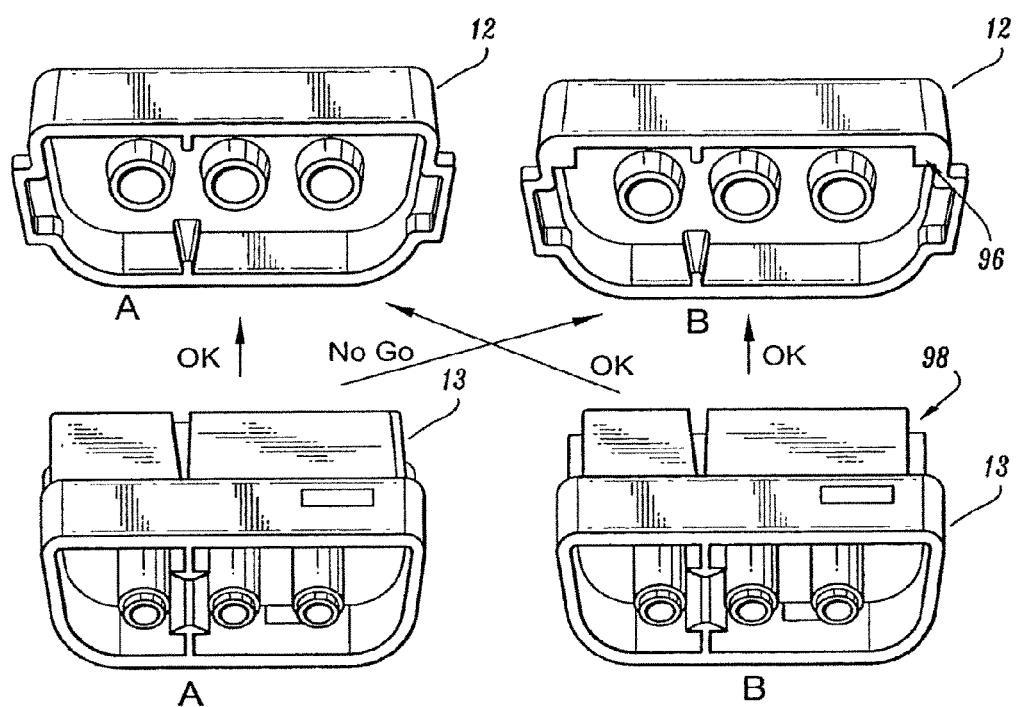
FIG. 14 is a schematic view of two embodiments of a first connector and two embodiments of a second connector.

Referring to FIG. 13, one embodiment includes a first connector 12 having an interference key 96 in the cavity 26 to prevent the first connector 12 from mating with legacy connector components. The second connector 14 includes a clearance space for the interference key 96. FIG. 14 schematically depicts the function of an interference key 96 to prevent connection of certain embodiments of a first connector 12 to certain embodiments of a second connector 13. For example, key slot 98 in second connector 13B provides clearance for interference key 96 in first connector 12B to facilitate mating one to the other. Second connector 13B can also be mated to certain first connectors such as 12A which do not include an interference key. Second connector 13A does not include a key slot and therefore can not be mated with first connector 12B. In at least one embodiment, second connector 13A is a legacy connector. In the illustrative embodiment, the interference key 96 in a non-compatible connector such as first connector 12B is used to prevent connection of the non-compatible connector to the legacy connector.

It will be understood that various modifications may be made to the embodiments disclosed herein. For example, the connector of the present disclosure may be used with various single and plural bladder compression sleeve devices including, for example, the compression sleeve described in U.S. Pat. No. 7,282,038, filed on Feb. 23, 2004 and entitled Compression Apparatus, the entire contents of which is hereby incorporated by reference herein. Therefore, the above description should not be construed as limiting, but merely as exemplification of the various embodiments. Those skilled in the art will envision other modifications within the scope and spirit of the claims appended hereto.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. A fluid connector apparatus adapted for use with a pneumatic compression apparatus for applying compression treatment to a user of the pneumatic compression apparatus, the pneumatic compression apparatus having a pneumatic characteristic when the fluid connector apparatus is in fluid communication with to the pneumatic compression apparatus and fluid is being delivered through the fluid connector apparatus, the connector apparatus comprising:

a first connector including a first plurality of fluid ports each having proximal ends and distal ends, at least one of the fluid ports comprising a coupling port having a port seat therein defining a fluid orifice, the first connector being adapted for nondestructive, releasable connection with a second connector at a distal end of the first connector;

a fluid conduit for each of the fluid ports configured for connecting to the pneumatic compression apparatus, each fluid conduit being connected to a proximal end of a respective one of the fluid ports, a first of the fluid conduits being connected to the coupling port;

a coupling fitting connected to the first fluid conduit and removably mated with the coupling port thereby to connect the first fluid conduit to the coupling port; and a valve disposed in the coupling port for movement relative to the coupling port, the valve being arranged in the coupling port for operatively engaging the coupling fitting when the coupling fitting is mated with the coupling port of the first connector so that movement of the coupling port and coupling fitting into mating connection is transmitted by the operative engagement of the coupling fitting with the valve to move and hold the valve away from the fluid orifice, the valve being disengaged from the coupling fitting when the coupling fitting and first conduit are removed from the coupling port of the first connector, the valve moving upon removal of the coupling fitting from the coupling port into engagement with the port seat to reduce a dimension of the fluid orifice without completely closing the fluid orifice to approximate the pneumatic characteristic of the pneumatic compression apparatus when the fluid connector apparatus is in fluid communication with the pneumatic compression apparatus and fluid is being delivered through the fluid connector apparatus.

2. A fluid connector apparatus as set forth in claim 1 wherein the valve includes a valve seat, the valve seat being engaged with the port seat when the coupling fitting is removed from the coupling port of the first connector and being spaced from the port seat when the coupling fitting is mated with the coupling port of the first connector.

3. A fluid connector apparatus as set forth in claim 2 wherein the port seat and valve seat are constructed to permit fluid flow through the fluid orifice, around the valve seat and past the port seat when the valve seat engages the port seat.

4. A fluid connector apparatus as set forth in claim 3 wherein at least one of the port seat and the valve seat has a slot therein sized and arranged to permit fluid flow past the valve seat and port seat when the valve seat engages the port seat.

5. A fluid connector apparatus as set forth in claim 4 wherein the slot is in the valve seat.

6. A fluid connector apparatus as set forth in claim 5 wherein the valve seat has plural slots sized and arranged to permit fluid flow past the valve seat and port seat when the valve seat engages the port seat.

7. A fluid connector apparatus as set forth in claim 6 further comprising a gasket disposed between the first and second connectors to facilitate fluid sealing between the first and second connectors.

8. A fluid connector apparatus as set forth in claim 1 in combination with said second connector and having a second plurality of fluid conduits, the second connector being adapted for connection to the first connector at a location remote from the connection of the coupling fitting to the first connector.

9. A fluid connector apparatus as set forth in claim 8 wherein the first connector includes a locking arm extending therefrom, the locking arm being adapted to releasably retain the first connector to the second connector.

10. A fluid connector apparatus as set forth in claim 9 wherein the second connector includes a slot for engaging the locking arm.

11. A fluid connector apparatus as set forth in claim 1 further comprising a pressurized fluid source.

12. A fluid connector apparatus as set forth in claim 1 wherein the coupling fitting includes an engagement portion that engages the valve upon connection of the coupling fitting with the coupling port and moves the valve away from the valve seat opening a fluid connection between the coupling fitting and said at least one of the fluid ports.

* * * * *